United States Patent [19]

Meek, deceased et al.

[11] Patent Number: Plant 5,338

[45] Date of Patent: Nov. 13, 1984

[54] CHRYSANTHEMUM PLANT NAMED GRENADINE

[75] Inventors: Jack M. Meek, deceased, late of Salinas, Calif.; Saundra J. Meek, executrix by, Canyon, Tex.; William E. Duffett, Salinas, Calif.; Grace H. Mack, New Canaan, Conn.

[73] Assignee: Grace H. Mack, New Canaan, Conn.

[21] Appl. No.: 422,149

[22] Filed: Sep. 23, 1982

[51] Int. Cl. ..... A01H 5/00

[52] U.S. Cl. ..... Plt./76

[58] Field of Search ..... Plt./76, 79

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum plant named Grenadine characterized by its flat capitulum form, decorative capitulum type, coral bronze ray floret color, diameter across face of capitulum up to 75 mm., short plant height, spreading branching pattern, average natural season flowering date of September 10, and averge flowering response period of seven (7) weeks in photoperiodic controlled short day programs.

3 Drawing Figures

The present invention comprises a new and distinct cultivar of *Chrysanthemum morifolium,* Ramat., hereinafter referred to by the cultivar name Grenadine.

Grenadine is a product of a planned breeding program which had the objective of creating cultivars with decorative capitulum type, short plant height, spreading branching pattern, durable inflorescence, seven (7) week controlled flowering response period, and coral bronze floret color under outdoor natural season conditions.

Grenadine was originated from a cross made in a controlled breeding program planned and executed by Grace H. Mack in New Canaan, Conn. in the year 1976. The female parent was Y4080, a bronze decorative which was an unnamed seedling from the cross of two unnamed seedlings (4570×0859). The male parent was 0519, a light bronze decorative which was an unnamed seedling from a cross of two unnamed seedlings (M221×Y4661).

Granadine was discovered and selected as a flowering plant within the progeny of the stated cross by J. Michael Meek Sept. 20, 1977 in an outdoor field in Salinas Calif. The first act of asexual reproduction of Grenadine was accomplished when vegetative cuttings were taken from the initial selection in 1977 in Salinas, Calif. by William E. Duffett. Horticultural examination of selected units initiated in 1978 has demonstrated that the combination of characteristics as herein disclosed for Grenadine are firmly fixed and are retained through successive generations of asexual reproduction.

Granadine has not been observed under all possible environmental conditions. The phenotype may vary significantly with variations in environment such as temperature, light intensity, and day length. The following observations, measurements, and comparisons describe plants grown in a field in Salinas, Calif.

Rooted cuttings were established in soil in one gallon containers maintained outdoors under the natural temperature and day length prevailing during July through September. Single pinching was practiced with all branches and buds retained.

The following traits have been repeatedly observed and are determined to be basic characteristics of Grenadine which in combination distinguish the chrysanthemum as a new and distinct cultivar:

(1) Flat capitulum form.
(2) Decorative capitulum type.
(3) Coral bronze ray floret color.
(4) Diameter across face of capitulum up to 75 mm.
(5) Short plant height.
(6) Spreading branching pattern.
(7) Average natural season flowering date of September 10.
(8) Average flowering response period of seven (7) weeks in photoperiodic controlled flowering programs.

The accompanying photographic drawings show typical inflorescence and foliage characteristics of Grenadine. Sheet 1 is a color photograph of Grenadine. Sheet 2 is a black and white photograph showing three views of the infloresescence of Grenadine. Sheet 3 is a black and white photograph showing the leaves of Grenadine at three stages of growth (mature, intermediate and immature).

Of the many commercially available cultivars known to the present inventors, the most similar existing cultivar in comparison to Grenadine is the cultivar Revere (U.S. Plant Pat. No. 4,005).

Reference is made to attached Chart A which compares certain characteristics of Grenadine with the same characteristics of Revere.

It will be noted that in comparison to Revere, Grenadine has different ray floret color, earlier average natural season flower date, and larger diameter across face of capitulum. The capitulum form, capitulum type, plant height, branching pattern, and plant spread of Grenadine are similar to those of Revere.

In the following description, color references are made to The Royal Horticultural Society Colour Chart. The color values were determined between 1:30 and 2:00 P.M. on Sept. 10, 1981 under 150 foot-candle light intensity at Salinas, Calif.

Botanical Classification: *Chrysanthemum morifolium,* Ramat., cv Grenadine.

INFLORESCENCE

Capitulum:

*Form.*—Flat.

*Type.*—Decorative.

*Permanence.*—2 To 3 weeks.

*Diameter across face.*—60 To 75 mm.

Corolla of Ray Florets:

*Color (abaxial).*—Approximately 2D at base of ray floret to 182C oxidizing to 182D and 181D on ray surface.

*Color (adaxial).*—179B oxidizing to 179C and 179D.

Reproductive organs:

*Androecium.*—Present disc florets.

*Gynoecium.*—Present both ray and disc florets.

Disc florets:

*Color.*—14A.

PLANT

General appearance: Spreading branching pattern; short height.

Foliage:

*Color* (abaxial).—Approximately 137A.

*Color (adaxial).*—Approximately 173A.

CHART A

COMPARISON OF GRENADINE AND REVERE

| | RAY FLORET | CAPITULUM FORM | AVERAGE NATURAL SEASON |
|---|---|---|---|

CHART A-continued

COMPARISON OF GRENADINE AND REVERE

| CULTIVAR | COLOR | AND TYPE | FLOWER DATE |
|---|---|---|---|
| GRENADINE | CORAL BRONZE | FLAT DECORATIVE | SEPTEMBER 10 |
| REVERE | BRONZE | FLAT DECORATIVE | SEPTEMBER 25 |

| CULTIVAR | PLANT HEIGHT | BRANCHING PATTERN AND SPREAD | DIAMETER ACROSS FACE OF CAPITULUM |
|---|---|---|---|
| GRENADINE | SHORT | SPREADING | 60 to 75 mm. |
| REVERE | SHORT | SPREADING | 55 TO 65 mm. |

COMPARISONS MADE OF PLANTS GROWN UNDER NATURAL SEASON OUTDOOR FIELD CONDITIONS IN SALINAS, CALIFORNIA

We claim:

1. A new and distinct cultivar of *Chrysanthemum morifolium,* Ramat., plant named Grenadine, as described and illustrated, and particularly characterized as to uniqueness by the combined characteristics of flat capitulum form, decorative capitulum type, coral bronze ray floret color, diameter across face of capitulum up to 75 mm., short plant height, spreading branching pattern, average natural season flowering date of September 10, and average flowering response period of seven (7) weeks in photoperiodic controlled short day programs.

* * * * *

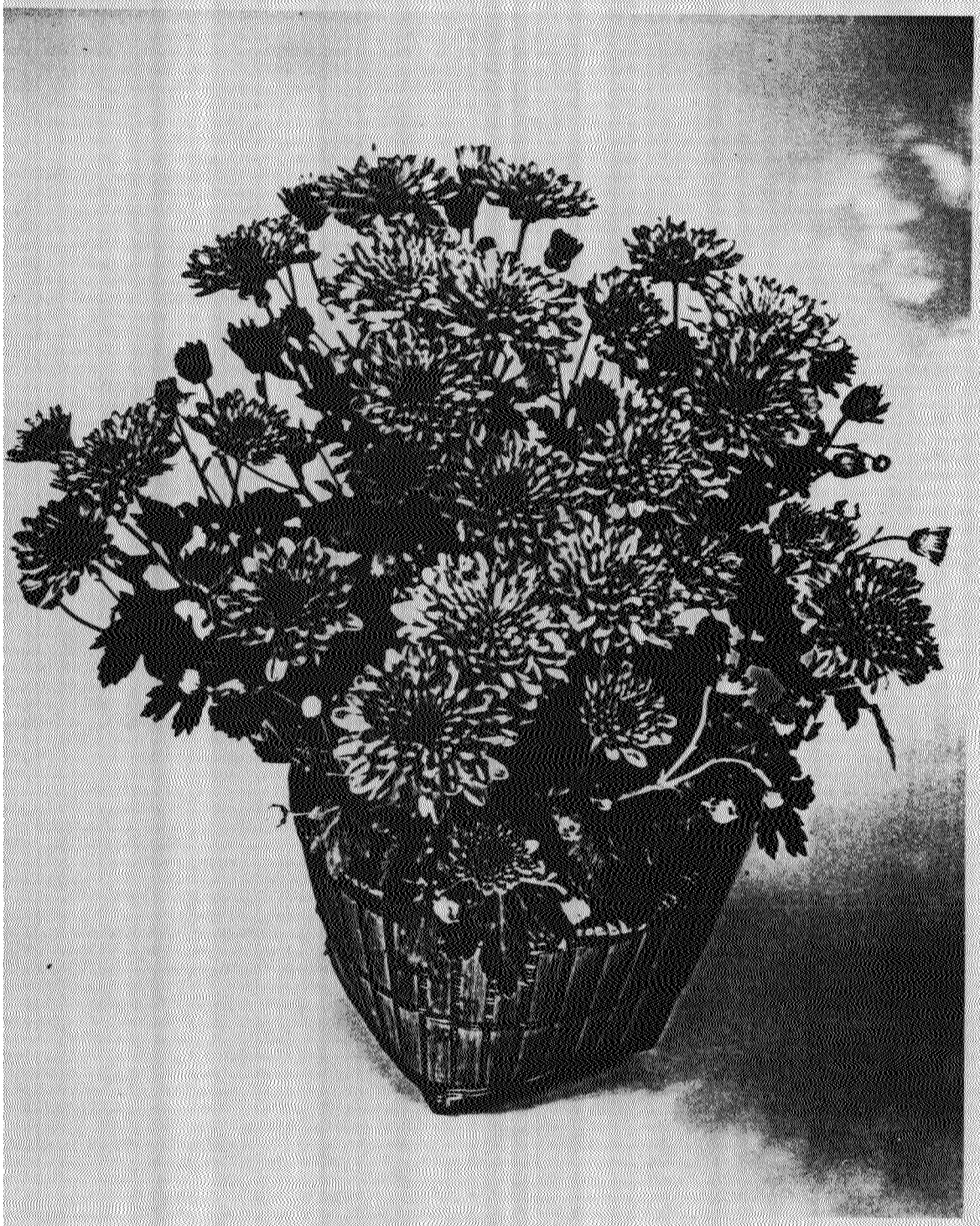

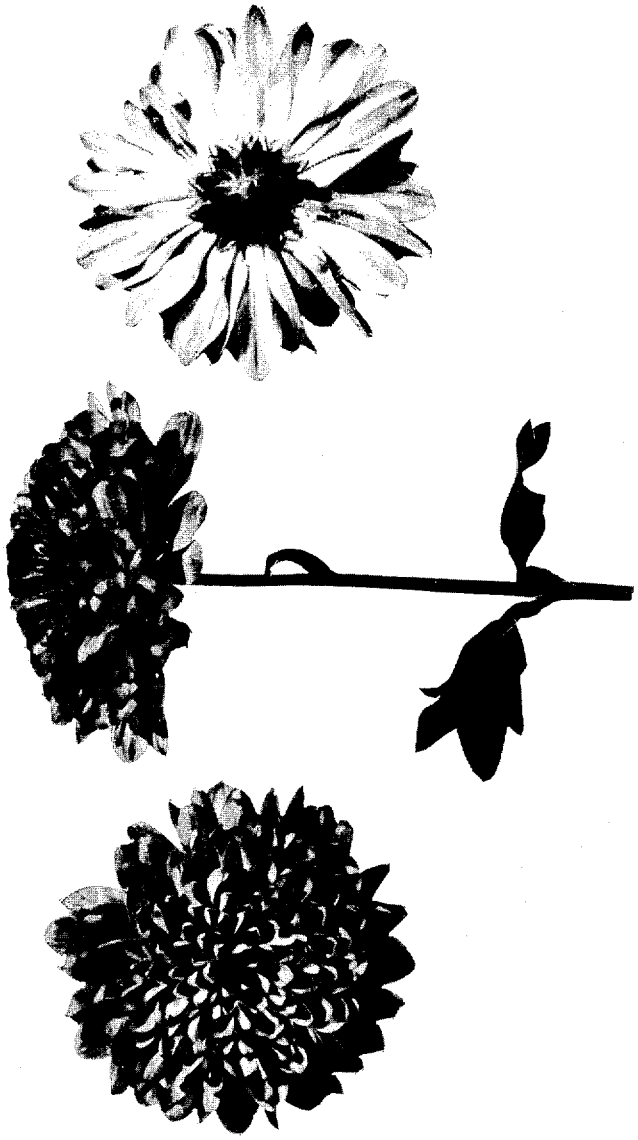

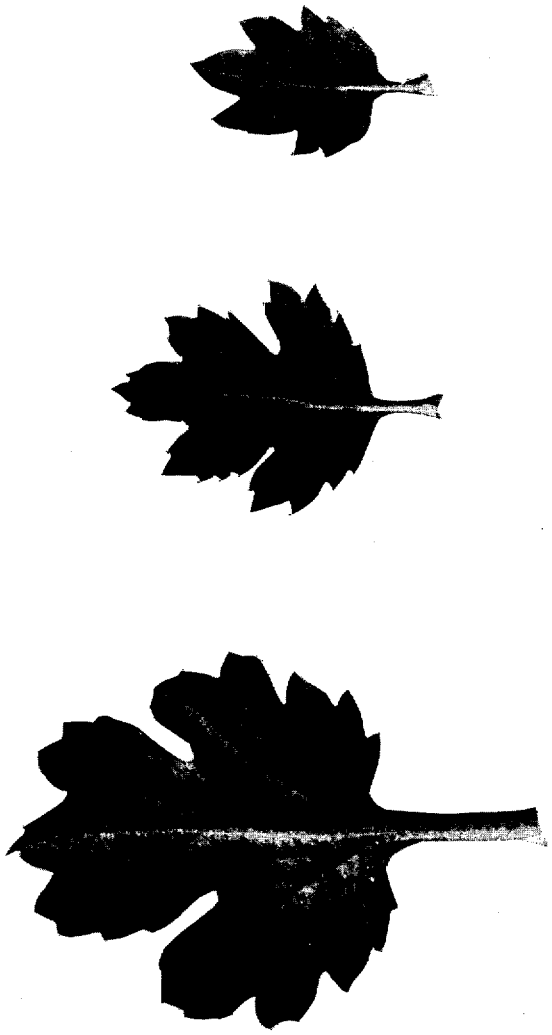

UNITED STATES PATENT OFFICE

CERTIFICATE OF CORRECTION

PATENT NO. : Plant Patent No. 5338

DATED : November 13, 1984

INVENTOR(S) : Jack M. Meek, deceased; Saundra J. Meek, executrix; William E. Duffett; Grace H. Mack It is certified that error appears in the above-identified patent and that said Letters Patent are hereby corrected as shown below:

In column 1, line 20, "Granadine" should be --Grenadine--.

In column 1, line 31, "Granadine" should be --Grenadine--.

In column 3, line 26, "Approximately 173A" should be --Approximately 137A--.

Signed and Sealed this

*Third* Day of *September 1985*

[SEAL]

*Attest:*

DONALD J. QUIGG

*Attesting Officer* *Acting Commissioner of Patents and Trademarks - Designate*